United States Patent [19]

Beck et al.

[11] 4,026,892
[45] May 31, 1977

[54] PROCESS FOR THE PREPARATION OF TETRACHLOROPYRIMIDINE

[75] Inventors: Gunther Beck, Leverkusen; Fritz Döring, Odenthal-Gloebusch; Hans Holtschmidt, Bergisch-Gladbach, all of Germany

[73] Assignee: Bayer Aktiengesellschaft, Leverkusen, Germany

[22] Filed: Oct. 28, 1975

[21] Appl. No.: 626,414

[30] Foreign Application Priority Data

Oct. 30, 1974  Germany .......................... 2451630

[52] U.S. Cl. ..................... 260/251 R; 260/465.5 R
[51] Int. Cl.² ....................................... C07D 239/20
[58] Field of Search ................................ 260/251 R

[56] References Cited

UNITED STATES PATENTS

| | | |
|---|---|---|
| 3,509,032 | 4/1970 | Beck et al. ............. 204/158 |
| 3,920,649 | 11/1975 | Beck et al. ............. 260/251 R |

*Primary Examiner*—Dolph H. Torrence
*Attorney, Agent, or Firm*—Burgess, Dinklage & Sprung

[57] ABSTRACT

A process for preparing tetrachloropyrimidine comprising reacting 2-cyano-1,2-(dichlorovinyl)-isocyanide-dichloride of the formula

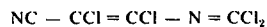

NC — CCl = CCl — N = CCl₂ with a Friedel-Crafts compound at an elevated temperature. The resulting tetrachloropyrimidine can be used as a reactive component for the preparation of reactive dyestuffs.

7 Claims, No Drawings

PROCESS FOR THE PREPARATION OF TETRACHLOROPYRIMIDINE

The subject of the present invention is a new process for the preparation of tetrachloropyrimidine.

The process is characterised in that 2-cyano-1,2-(dichlorovinyl)-isocyanide-dichloride of the formula $$NC-CCl=CCl-N=CCl_2 \quad (I)$$

is reacted with Friedel-Crafts compounds at elevated temperatures.

In general, the reaction is carried out in the temperature range from 150° to 250° C, preferably between 170° and 230° C.

Suitable Friedel-Crafts compounds are described, for example, in "Friedel Crafts and Related Reactions", Volume I, page 201. The following may be mentioned as examples: $AlCl_3$, $AlBr_3$, $BeCl_2$, $CdCl_2$, $ZnCl_2$, $BF_3$, $BCl_3$, $BBr_3$, $GaCl_3$, $TiCl_4$, $TiBr_4$, $ZrCl_4$, $SnCl_4$, $SnBr_4$, $SbCl_5$, $SbCl_3$, $FeCl_3$ and $UCl_4$.

$AlCl_3$ or $FeCl_3$ are particularly preferred.

In general, the Friedel-Crafts compounds are employed in an amount of 0.1 to 50 percent by weight, preferably 1 to 20 percent by weight, relative to (I).

2-Cyano-1,2-(dichlorovinyl)-isocyanide-dichloride of the formula (I), used as the starting material, is prepared as follows:

Starting from N-(2-cyanoethyl)-formamide (II), obtainable in a known manner (French Patent Specification 976,959) from acrylonitrile and formamide, 2-cyano-1,1,2,2-(tetrachloroethyl)-isocyanide-dichloride of the formula (III) is next prepared in accordance with the equation

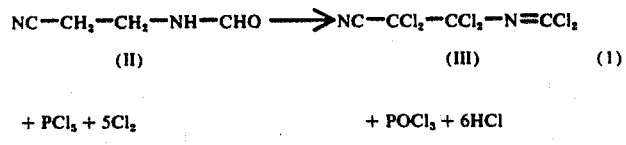

and this is then dechlorinated with phosphorus according to the equation below, to give (I).

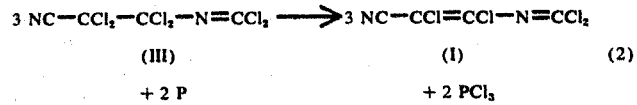

Further details are to be found in the experimental section.

To carry out the process according to the invention, the liquid starting compound of the formula (I) is mixed with, preferably, 1 – 20 percent by weight of a Friedel-Crafts compound, preferably iron-(III) chloride or aluminium chloride (of course mixtures of different Friedel-Crafts compounds are also suitable) and heated to the stated temperature range, preferably to 170° – 230° C, until the tetrachloropyrimidine has been formed.

The time required naturally depends on the nature and amount of the Friedel-Crafts compound and on the reaction temperature. In general, it is of the order of magnitude of one to 50 hours.

Of course the process can also be carried out continuously.

It is extremely surprising that such severe reaction conditions as, for example, heating for four hours at 200° C in the presence of such particularly active Friedel-Crafts compounds as $FeCl_3$ or $AlCl_3$ leads to no elimination of cyanogen chloride from the starting material (I), which is present as a cis-trans mixture; such elimination is entirely possible with isocyanide-dichlorides ("Angw. Chemie" 81. 18).

It was already known (DT-OS (German Published Specification) 2,307,863) to obtain tetrachloropyrimidine, starting from N-(2-cyanoethyl)-formamides of the formula

wherein
R denotes a radical which can be split off under the reaction conditions, in a one-stage reaction, by treatment with acid chlorides and chlorine.

However, this process has the disadvantage that major amounts of chlorinated alkanes (for example, when using the particularly preferred N-(2-cyanoethyl)-N-ethyl-formamide, about 0.5 tonne of chlorinated ethanes per tonne of tetrachloropyrimidine) are produced, and the removal of these is expensive.

In the present process of the invention, starting from N-(2-cyanoethyl)-formamide of the formula (II), admittedly three reaction steps are required, but all of these take place with good yields. The last reaction step, of converting (I) to the tetrachloropyrimidine, takes place practically quantitatively, and the second reaction step, of converting compound (III) to compound (I) (equation (2) ) takes place with over 80% yield.

The first reaction step, of converting compound (II) to compound (III) (equation (1) ) admittedly only gives a yield of, for example, about 65% of theory of 2-cyano-1,1,2,2-(tetrachloroethyl)-isocyanide-dichloride (III), as can be seen from the experimental example. However, the subsequently produced tetrachloropyrimidine gives a quasi-increase to about 75%. Since it is inert, under the conditions described, to phosphorus and Friedel-Crafts compounds, isolation of (III) is not necessary.

2,4,5-Trichloropyrimidine (molar yield about 9%), which is formed as a second by-product, can also be converted to tetrachloropyrimidine, by gas phase chlorination (British Patent Specification 1,201,228). For this purpose, it is possible either to isolate it immediately after completion of the first reaction stage, which can be done conveniently by distillation as it is the lowest-boiling component, and then be post-chlorinated, or it can, like the tetrachloropyrimidine, be allowed also to pass through all three stages and only be post-chlorinated at the end, with or without prior removal of tetrachloropyrimidine by distillation. Since the gas phase chlorination according to British Patent Specification 1,201,228 takes place practically quantitatively, the quasi yield of the first reaction stage is increased by about a further 9 mol percent, to about 84 mol percent, if one wishes to carry out this gas phase chlorination.

Tetrachloropyrimidine can be used as a reactive component for the preparation of reactive dyestuffs (compare Belgian Patent Specification 578,933).

EXAMPLE 1 a. 8.0 g of 2-cyano-1,2-(dichlorovinyl)-isocyanide-dichloride and 0.80 g of iron (III) chloride are kept for 4 hours in an oil bath at 200° C. The analysis of the reaction product by gas chromatography shows that it consists to the extent of 99.3% of tetrachloropyrimidine, which is identical in all properties with an authentic sample.

b. The procedure followed is analogous to (a), with the difference that instead of 0.80 g of iron (III) chloride, 0.80 g of aluminium chloride is used. According to the gas chromatogram, the reaction product consists to the extent of 98.4% of tetrachloropyrimidine.

EXAMPLE 2

8.0 g of 2-cyano-1,2-(dichlorovinyl)-isocyanide-dichloride and 0.40 g of aluminium chloride are kept for 10 hours in an oil bath at 200° C. Analysis of the reaction product by gas chromatography shows that it consists to the extent of 98.5% of tetrachloropyrimidine.

EXAMPLE 3

20.0 g of 2-cyano-1,2-(dichlorovinyl)-isocyanide-dichloride and 0.40 g of aluminium chloride are kept for about 20 hours under reflux (about 215°– 220° C), during which time the reaction mixture gradually assumes a dark brown colour. Distillation at 100° – 108° C/15 mm Hg leaves a residue of 5 g. The colourless distillate (14 g) consists, according to analysis by gas chromatography, to the extent of 36.0% of starting material and to the extent of 63.8% of tetrachloropyrimidine.

2-Cyano-1,2-(dichlorovinyl)-isocyanide-dischloride, used as the starting material, is obtained as follows:

434 g (1.5 mols) of 2-cyano-1,1,2,2-(tetrachloroethyl)-isocyanide-dichloride and 60 g (1.93 mols) of red finely powdered phosphorus are kept at a temperature of 205° to 215° C for about 5 hours under an about 60 cm long silvered column with dephlegmator, whilst continuously distilling off the phosphorus trichloride formed. Subsequent fractionation at 99° to 101° C/15 mm Hg gives 267 g (corresponding to 81.6% of theory) of 2-cyano-1,2-(dichlorovinyl)-isocyanide-dichloride of the formula

as a cis-trans mixture in the form of a colourless liquid. The empirical formula $C_4Cl_4N_2$ is confirmed by the mass spectrum.

EXAMPLE 4

1,955 g of a mixture of tetrachloropyrimidine and 2-cyano-1,1,2,2-(tetrachloroethyl)-isocyanide-dichloride (1,421 g ≙ 4.92 mols, according to the gas chromatogram) and 200 g (6.45 mols) of red, finely powdered phosphorus are kept at an internal temperature of between 210° and 200° C for 2.5 hours under a 30 cm long silvered Vigreux column with dephlegmator, in the course of which phosphorus trichloride distils off. After stripping off the phosphorus trichloride, all constituents of the reaction mixture which distil in a waterpump vacuum are collected. According to the gas chromatogram, the distillate consists of tetrachloropyrimidine and 2-cyano-1,2-(dichlorovinyl-isocyanide-dichloride (925 g, corresponding to 86% of theory).

PREPARATION OF THE STARTING MATERIAL 98 g (1 mol) of N-(2-cyanoethyl)-formamide are added dropwise over the course of 2 hours to a suspension, saturated with chlorine, of 230 g (1.1 mols) of phosphorus pentachloride in 350 ml of phosphorus oxychloride at about 20° C in a four-neck flask equipped with a stirrer, thermometer, reflux condenser, gas inlet tube and dropping funnel, and at the same time excess chlorine is passed in at a rate such that the off-gas is always greenish in colour. Thereafter, the mixture is heated to a reflux temperature of 112° C over the course of 2.5 hours, whilst continuing to pass in excess chlorine. After cooling POCl₃ is distilled off under a waterpump vacuum, through a bridge, until the internal temperature is 50° C. After replacing the distillation bridge by a reflux condenser, the temperature is raised to 190° C (reflux) over the course of 1.5 to 2 hours, in a stream of chlorine, and chlorination is continued for a further 7 hours at an oil bath temperature of 220° C, the internal temperature rising to 203° C at the end of the chlorination. After cooling, sulphur dioxide is passed in for about half an hour at 120° – 130 ° C on order to destroy the excess phosphorus pentachloride in accordance with the equation $$PCl_5 + SO_2 \rightarrow POCl_3 + SOCl_2.$$

Thereafter, the fraction which starts to distil at 100° C/16 mm Hg is collected and distillable material is thoroughly removed up to an oil bath temperature of 250° C. Residue 20 g. The distillate (231 g) consists, according to analysis by gas chromatography, of the three compounds 2,4,5-trichloropyrimidine (7.2%), tetrachloropyrimidine (9.9%) and 2-cyano-1,1,2,2-(tetrachloroethyl)-isocyanide-dichloride (81.0%). Accordingly, the yield of 2-cyano-1,1,2,2-(tetrachloroethyl)-isocyanide-dichloride, as determined by gas chromatography, is 64.7% of theory. The compound is prepared in a pure form by fractional distillation through a column. Boiling point 128° C/20 mm Hg. Structural formula:

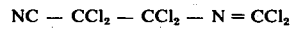

The composition $C_4Cl_6N_2$ is confirmed by the mass spectrum.

We claim:

1. Process for the preparation of tetrachloropyrimidine, characterised in that 2-cyano-1,2-(dichlorovinyl)-isocyanide-dichloride of the formula

is reacted with Friedel-Crafts compounds at a temperature of 150° to 250° C.

2. Process according to claim 1, characterised in that the reaction is carried out at 170° to 230° C.

3. Process according to claim 1, characterised in that the Friedel-Crafts compounds are employed in an amount of 0.1 to 50 percent by weight, relative to 2-cyano-1,2-(dichlorovinyl)-isocyanide-dichloride.

4. Process according to claim 1, characterised in that the Friedel-Crafts compounds are employed in an amount of 1 to 20 percent by weight.

5. Process according to claim 1, characterised in that iron-(III) chloride or aluminium chloride are used as Friedel-Crafts compounds.

6. Process for the preparation of tetrachloropyrimidine, characterised in that N-(2-cyanoethyl)-formamide, in phosphorus oxychloride, is first reacted simultaneously with at least 1 mol of phosphorus pentachloride or a corresponding mixture of phosphorus trichloride and chlorine and excess chlorine, at temperatures of up to about 200° C, to give 2-cyano-1,1,2,2-(tetrachloroethyl)-isocyanide-dichloride, the 2-cyano-1,1,2,2-(tetrachloroethyl)-isocyanide-dichloride is then reacted, at about 200° to 220° C, with at least the stoichiometrically required amount of phosphorus to give 2-cyano-1,2-(dichlorovinyl)-isocyanide-dichloride of the formula $$NC - CCl = CCl - N = CCl_2$$

and thereafter the 2-cyano-1,2-(dichlorovinyl)-isocyanide-dichloride is reacted with Friedel-Crafts compounds at a temperature of 150° –250° C.

7. Process according to claim 1 wherein the catalyst is selected from the group consisting of $AlCl_3$, $AlBr_3$, $BeCl_2$, $CdCl_2$, $ZnCl_2$, $BF_3$, $BCl_3$, $BBr_3$, $GaCl_3$, $TiCl_4$, $TiBr_4$, $ZrCl_4$, $SnCl_4$, $SnBr_4$, $SbCl_5$, $SbCl_3$ $FeCl_3$ and $UCl_4$.

* * * * *

UNITED STATES PATENT AND TRADEMARK OFFICE
CERTIFICATE OF CORRECTION

PATENT NO. : 4,026,892
DATED : May 31, 1977
INVENTOR(S) : Gunther Beck et al

It is certified that error appears in the above-identified patent and that said Letters Patent are hereby corrected as shown below:

Column 1, line 21, "GaCl 3" should read -- $GaCl_3$ --.

Column 3, line 47, "dischloride" should read -- dichloride --.

Column 4, line 36, "on order" should read -- in order --.

Column 5, line 15-16, (Claim 6, line 5-6), insert parentheses around "or a corresponding mixture of phosphorus trichloride and chlorine".

Signed and Sealed this

Sixth Day of December 1977

[SEAL]

Attest:

RUTH C. MASON
Attesting Officer

LUTRELLE F. PARKER
Acting Commissioner of Patents and Trademarks